US010705073B2

(12) United States Patent
Keller

(10) Patent No.: US 10,705,073 B2
(45) Date of Patent: Jul. 7, 2020

(54) METHOD FOR IDENTIFYING OF A BIOLOGICAL SAMPLE OF A MAMMAL, COMPOSITION FOR USE IN THIS METHOD AND KIT FOR PERFORMANCE OF THIS METHOD

(71) Applicant: Ruprecht Keller, Schleiden (DE)

(72) Inventor: Ruprecht Keller, Schleiden (DE)

( * ) Notice: Subject to any disclaimer, the term of this patent is extended or adjusted under 35 U.S.C. 154(b) by 0 days.

(21) Appl. No.: 16/446,172

(22) Filed: Jun. 19, 2019

(65) Prior Publication Data
US 2019/0302098 A1 Oct. 3, 2019

Related U.S. Application Data

(62) Division of application No. 14/727,281, filed on Jun. 1, 2015.

(30) Foreign Application Priority Data
Jun. 18, 2014 (DE) ........................ 10 2014 008 723

(51) Int. Cl.
*G01N 33/493* (2006.01)
*G01N 33/58* (2006.01)
*G01N 33/94* (2006.01)

(52) U.S. Cl.
CPC ........... *G01N 33/493* (2013.01); *G01N 33/58* (2013.01); *G01N 33/9486* (2013.01); *G01N 2560/00* (2013.01); *Y10T 436/13* (2015.01)

(58) Field of Classification Search
CPC .................................................... G01N 33/493
See application file for complete search history.

(56) References Cited

U.S. PATENT DOCUMENTS

| | | | |
|---|---|---|---|
| 4,017,616 A | 4/1977 | Gomez et al. |
| 4,953,562 A | 9/1990 | Rosen et al. |
| 5,024,231 A | 6/1991 | Feldschuh et al. |
| 5,039,616 A | 8/1991 | Copelan et al. |
| 5,093,265 A | 3/1992 | Portman et al. |
| 5,179,027 A | 1/1993 | Fisher et al. |
| 5,206,030 A | 4/1993 | Wheatley et al. |
| 5,393,054 A | 2/1995 | Rouffer |
| 5,531,682 A | 7/1996 | Mazer et al. |
| 5,643,728 A | 7/1997 | Slater et al. |
| 6,068,981 A | 5/2000 | Rittenberg et al. |
| 6,303,102 B1 | 10/2001 | Schlichte |
| 6,440,667 B1 | 8/2002 | Fodor et al. |
| 7,062,312 B2 | 6/2006 | Gonzales et al. |
| 7,115,301 B2 | 10/2006 | Sheu et al. |
| 7,674,625 B2 | 3/2010 | Gauchel |
| 7,820,444 B2 | 10/2010 | Keller et al. |
| 7,858,607 B2 | 12/2010 | Mamchur |
| 7,972,859 B2 | 7/2011 | Eastwood et al. |
| 8,420,400 B2 | 4/2013 | Hayward et al. |
| 9,226,874 B2 | 1/2016 | Siegel |
| 2002/0095072 A1 | 7/2002 | Gonzales et al. |
| 2004/0037869 A1 | 2/2004 | Cleverly et al. |
| 2004/0016653 A1 | 8/2004 | Keller |
| 2005/0008762 A1 | 1/2005 | Sheu et al. |
| 2006/0029661 A1 | 2/2006 | Radhakrishnan |
| 2006/0154297 A1 | 7/2006 | Gauchel |
| 2007/0196927 A1 | 8/2007 | Gandfils et al. |
| 2007/0298502 A1 | 12/2007 | Eastwood et al. |
| 2009/0075261 A1 | 3/2009 | Hayward et al. |
| 2009/0238778 A1 | 9/2009 | Mordas et al. |
| 2010/0006750 A1 | 1/2010 | Kolbjorn |
| 2011/0182807 A1 | 7/2011 | Fuisz et al. |
| 2011/0217243 A1 | 9/2011 | Siegel |
| 2011/0299081 A1 | 12/2011 | Manka et al. |
| 2015/0369794 A1 | 12/2015 | Keller |

FOREIGN PATENT DOCUMENTS

| | | |
|---|---|---|
| DE | 10130321 A1 | 1/2003 |
| DE | 10360924 A1 | 7/2005 |
| DE | 10112470 B4 | 2/2008 |
| EP | 1410014 A1 | 4/2004 |
| EP | 1462118 A1 | 9/2004 |
| EP | 1563311 A2 | 8/2005 |
| EP | 2502621 A1 | 9/2012 |
| GB | 2271848 A | 4/1994 |
| GB | 2320960 A | 7/1998 |
| JP | 2000-028614 A | 1/2000 |
| WO | 1998/012557 A1 | 3/1998 |
| WO | 1998/014275 A1 | 4/1998 |
| WO | 1998/018003 A1 | 4/1998 |
| WO | 1998/036775 A1 | 7/1998 |
| WO | 1999/017747 A1 | 4/1999 |
| WO | 1999/056789 A1 | 11/1999 |
| WO | 2000/074781 A1 | 12/2000 |
| WO | 2002/056919 A2 | 7/2002 |
| WO | 2002/075307 A1 | 9/2002 |
| WO | 2004/046715 A2 | 6/2004 |

(Continued)

OTHER PUBLICATIONS

Ehrig et al. Nephrol Dial Transplant, 1999, 14:190-192.*
Schneider et al. Eur Addict Res, 2008, 14:186-189.*
Larsen et al., "Accumulation of magnetic iron oxide nanoparticles coated with variably sized polyethylene glycol in murine tumors," Nanoscale, 2012, 4:2353-2361.
Bhatia et al., 1966, "Dye-Polyethylene Glycol 6000 Interactions in Filmcoating Solutions and Their Effect on Color Uniformity," J. of Pharmaceutical Sciences, v. 55, No. 10, 1116-1121.
Bjamasonetal., 1995, "Intestinal Permeability: AnOverview," Gastroenterology, v. 108,p. 1566-1581.
Eaton et al., 1995, "Gut permeability measured by polyethylene glycol absorption in abnormal gut fermentation as compared with food intolerance," J. Royal Soc. Med., vol. 88: 63-66.
Young et al., 1990, "Measurement of Polyethylene Gloycol 400 in Urine by Direct-Injection High-Performance Liquid Chromatography," Clin. Chem., vol. 36/10, p. 1800-1802.

(Continued)

*Primary Examiner* — Bin Shen
(74) *Attorney, Agent, or Firm* — K&L Gates LLP

(57) ABSTRACT

The invention relates to methods through which a biological sample of a mammal can be precisely assigned and identified, comprising administering at least one essentially nonmetabolizable marker substance and a dye.

13 Claims, No Drawings

(56) References Cited

FOREIGN PATENT DOCUMENTS

| WO | 2007/095622 A2 | 8/2007 |
|---|---|---|
| WO | 2009/136763 A1 | 11/2009 |
| WO | 2011/032584 A1 | 3/2011 |
| WO | 2011/091413 A1 | 7/2011 |
| WO | 2013/078403 A1 | 5/2013 |
| WO | 2014/058582 A1 | 4/2014 |
| WO | 2014/210434 A1 | 12/2014 |

OTHER PUBLICATIONS

B.L. Milman, Chemical Identification and its Quality Assurance, 23 (Springer-Verlag Berlin Heidelberg, 1'1 ed. 2011), p. 23-39.
ChemIndustry.m "Polyethylene Glycol: Chemical Product Info", retrieved from the internet at http://chemindustry.ru/Polyethylene Glycol.php on Feb. 27, 2018.
Wilson et al., "Urinary monitoring of saccharin and acesulfame-K as biomarkers of exposure to these additives" Food Additives & Contaminants 16(6): 227-238.
Knauer Application Note: "Determination of preservatives in food-stuffs and cosmetics" HPLC SMB Osmometry, updated Aug. 2010.
Zoulias et al., "Effect of sugar replacement by polyols and acesulfame-K on properties of low-fat cookies" J. Sci. Food Agri. 80: 2049-2056.
Chauhan et al., Indian J of Pharmaceutical Sciences, 2007, 748-752.
Rounds et al., J Fluoresc., 2007, 17:57-63.
German Office Action dated Jul. 28, 2014 of German application No. 10 2014 008 723.9 (English translation only).
Latham, M.C. et al. D-xylose as tracer in dietary supplements, 1971, The Lancet, vol. 298(7721), pp. 405-406.
Donovan et al. 1990, Pharm. Res. vol. 7(9), pp. 863-868.
He et al. 1998, J. Phar. Sci. vol. 87(5), pp. 626-633.
Miki et al., "Rapid and simultaneous quantification of rhamnose, mannitol, and lactulose in urine by HPLC for estimating intestinal permeability in pediatric practice," 1996 Clin. Chem. vol. 42(1), pp. 71-75.
Bjarnason et al., "Comparison of four markers of intestinal permeability in control subjects and patients with coeliac disease," 1994, Scand. J. Gastroenterol. vol. 29, pp. 630-639.
Philipsen et al., 1998 Eur. J. Clin. Invest. vol. 18, pp. 139-145.
Ukabam et al. "Small intestinal permeability to mannitol, lactulose, and polyethylene glycol 400 in celiac disease," 1984 Digestive Diseases and Sci. vol. 29(9), pp. 809-816.
Opposition of EP 02732486: "Communication of a notice of opposition" dated Sep. 27, 2007.
Opposition of EP 02732486: "response to the Opposition" dated Dec. 18, 2007.
Opposition of EP 02732486: "Summons to attend oral proceedings" dated Aug. 19, 2010.
Opposition of EP 02732486: "Brief Communication" dated Sep. 29, 2010.
Opposition of EP 02732486: "Second Reply to the Summons to Attend Oral Proceedings" dated Sep. 20, 2010.
Opposition of EP 02732486: "Minutes of the oral proceedings before the Opposition Division" dated Oct. 20, 2010.
Opposition of EP 02732486: "Interlocutory decision in Opposition proceedings" dated Apr. 14, 2011.
Opposition of EP 02 732486: "Acknowledgement of receipt of the document specified above" dated Apr. 14, 2011.
Opposition of EP 02732486: "Decision to maintain the European patent in amended form" dated May 18, 2012.
M. K. Modasiya & V. M. Patel, "Studies on solubility of curcumin" International Journal of Pharmacy & Life Sciences, vol. 3, Issue 3, 1490-97 (Mar. 2012).
Van Rossum, J. M., "Kinetics of Drug Action," Handbook of Experimental Pharmacology, Springer, (1977), vol. 47.
Bernd Huppertz, et al., "Urine labeling with orally applied marker substances in drug substitution therapy", Clinical Chemistry and Laboratory Medicine, DE, (Jan. 7, 2004), vol. 42, No. 6, doi:10.1515/CCLM.2004.107, ISSN 1434-6621, pp. 621-626.
Gauchel G, et al., "Clinical use of polyethylene glycols as marker substances and determination in urine by liquid chromatography", Journal of Chromatography B: Biomedical Sciences & Applications, Elsevier, Amsterdam, NL, (Apr. 25, 2003), vol. 787, No. 2, doi:10.1016/S1570-0232(02)00925-X, ISSN 1570-0232, pp. 271-279.

\* cited by examiner

METHOD FOR IDENTIFYING OF A BIOLOGICAL SAMPLE OF A MAMMAL, COMPOSITION FOR USE IN THIS METHOD AND KIT FOR PERFORMANCE OF THIS METHOD

CROSS-REFERENCE TO RELATED APPLICATIONS

The present application is a divisional of U.S. patent application Ser. No. 14/727,281, filed Jun. 1, 2015, which claims priority to German Patent Application No. DE 10 2014 008 723.9, filed Jun. 18, 2014, the entire contents of which are incorporated herein by reference and relied upon.

BACKGROUND

The present invention relates to a method through which a biological sample of a mammal can be precisely assigned and identified, the biological sample having been taken as, for example, urine of the mammal. The assignable and identified urine sample can then be investigated for an analyte. The object of the invention also is a kit for performance of this method as well as a composition comprising at least one essentially non-metabolizable marker substance and a dye, usable in the method and the kit. This application also concerns a method that makes it possible to determine whether the sample was manipulated in a particular way.

Diagnostic methods, methods for monitoring the course of a therapeutic procedure, prophylactic routine examinations, as well as forensic medical examinations on humans generally entail analytical laboratory examination of samples, like blood or serum samples that were taken from the subjects, as well the examination of excretions of subjects, for example, urine. Considering the number of available veterinary diagnostic and therapeutic methods, a wide variety of analytical methods with animal samples are common practice nowadays. It is precisely the problems that have occurred in conjunction with large-scale livestock agriculture, like BSE diseases due to the feeding of meat and bone meal or admixing of legally banned feed additives in the form of hormone and/or antibiotic preparations in animal feed, that require expansion of regular control examinations in animal herds in agriculture.

It is then beyond question that any analytical examination of a sample is only useful and effective if the results obtained as a result of the examination can also be assigned without doubt to the corresponding donor of the sample in order to then be able to initiate the correct subsequent measures in evaluating the experimental results.

New analysis and test methods are continuously being developed in the course of scientific-technical progress. Progress in molecular biology, for example, permits the use of a number of detection methods based on DNA analysis through which certain diseases in humans or animals can be diagnosed.

A number of newer analysis and detection methods also find application in forensic medicine and are being created as a result of increasingly more demanding tasks of forensic medicine, like specific test methods to detect doping substances in performance athletes or to detect drugs in vehicle drivers.

High requirements on the technical equipment and the personnel of laboratories performing these studies are imposed because of the number of employed analysis methods and their complexity. Generally a larger number of samples are examined simultaneously with modern analysis instruments so that the problem of confusion of samples necessarily occurs, which leads to false assignment of the examination results to the sample donor. This problem is not new and is also further intensified precisely by the enormous development of new analysis methods and the growing demand for their use.

Since the effects of confusion or substitution of samples being analyzed are different but generally undesired, there are already an entire series of proposals to solve this problem.

These solutions essentially concern improved organization of the work procedure in an investigation laboratory, in which the hazard of confusion of samples is to be kept as low as possible by complying with certain behavioral rules. However, since a number of work steps are conducted by laboratory personnel in these analysis methods, confusion due to human error cannot be completely ruled out.

With this in mind, computer-controlled monitoring of analysis steps to be conducted with the sample is still widely used, for example, by marking sample containers with a computer-readable code so that the corresponding sample can be followed during the entire investigation process, beginning with receipt of the sample and including workup and storage of the experimental results. This computer-monitored and controlled analysis of samples therefore permits a high number of parallel determinations of different samples without a noticeable hazard of confusion.

However, it is clear to one skilled in the art that even such a system, designed for monitoring of samples being investigated in a laboratory and assignment of the test results to these samples and therefore to the sample donors, still cannot fully rule out confusion or substitution, since insufficient marking of the samples or the test results pertaining to them can still occur.

The outlined problem of confusion or substitution of samples is further intensified especially in areas of application in which the test results can be used as incriminating evidence against the sample donor or, in the case of a sample originating from an animal, against the owner of the animal. In these cases there is a particular interest among subjects or owners to manipulate test samples in order to prevent the creation of incriminating evidence.

However, it is precisely in these cases that unambiguous assignment of test results to the sample donor acquires special significance, since specific legal standards can only be accomplished in this way.

The solutions already existing in the prior art with respect to this problem of preventing manipulation of the sample exclusively concern monitoring of sampling. For example, it is common practice to monitor urine sampling of subjects participating in methadone therapy.

However, even worked out monitoring and observation of subjects during, for example, taking of urine samples will not fully prevent substitution of samples. Thousands of heroin addicts in Germany are already being treated with methadone. A sharp rise in this figure is expected in the future. Since methadone patients frequently take other narcotics as well as barbiturates and tranquilizers, monitoring of the substances taken by patients is therapeutically essential.

According to the guidelines for performing methadone therapy, the urine must be checked at least once a week or, under certain conditions, even more frequently. Furnishing a urine sample under observation is generally not possible in ordinary medical practices, since only a small lavatory is available and sufficient male medical personnel generally are not available to accompany male methadone patients.

Setting up appropriate lavatories for sample taking under observation requires considerable financial expense.

Because of the frequently established manipulation of furnished urine samples, increasingly work is underway to develop analysis methods to detect drugs in sputum. Although a sputum sample can be obtained without an infringing intervention or violation of the privacy of the subject, in contrast to use of blood, plasma or urine as test samples, the hazard of willful confusion or malicious manipulation of the sample cannot be prevented, despite everything.

U.S. Pat. No. 5,179,027 provides a method for checking the origin and completeness of urine samples and includes: taking of an amount of a first and second chemical marker by an individual, in which the first marker is excreted quantitatively and the second marker excreted in measurable amounts via the urine in order to confirm the completeness and correctness of the origin of the urine during later chemical analysis; obtaining a urine sample of said individual within a period after intake, which is sufficient in order to permit the required amounts of the first and second marker chemicals to be excreted via the urine; documentation of the time of intake, the amount and identity of the taken marker and the identity of the individual; and finally analysis of the sampled urine in order to determine the amounts of the first and second chemical markers in it in order to check the origin and completeness of the urine sample.

Another method is described in EP 1 410 014 A1. In this method a biological sample is clearly assigned to a mammal by administering at least one essentially non-metabolizable substance (marker) orally to the mammal with a liquid containing the marker. The liquid that contains the marker is referred to as marker liquid or marker solution and the method is referred to as method with endogenous marker. After a period sufficient for the marker substance to reach the location of sampling, a biological sample is taken from the mammal, which must contain the administered marker substance. The marker substance is selected from the chemical classes of isoprenoids, lipids, saccharides, polyols, polyethylene glycols or their derivatives. The method is particularly suited for identification of urine samples. The liquid that is administered to the animal with the marker is referred to subsequently as marker liquid.

However, it has been found that many subjects attempt to circumvent the method described in EP 1 410 014 A by retaining a small amount of the marker solution being drunk in the mouth, for example, with a cotton ball and introducing this to clean foreign urine so that the foreign sample contains the correct marker. To recognize this manipulation a metabolizable substance can be added to the marker solution. Such a method is proposed, for example, in EP 1 563 311. There—a marker substance is described which metabolizes in the body so that it is no longer present in body excretions, for example, urine, is additionally administered to the subject. When the subject attempts to manipulate assignment by spitting the marker solution retained in the mouth into foreign urine, the marker substance can be detected in the foreign urine and the corresponding manipulation therefore detected.

If metabolizable substances are mixed with the marker solution as "saliva marker", which are ordinarily not present in urine, their detection in the urine can reliably recognize a deception attempt. These metabolizable substances can be sucrose, propylene glycol esters of fatty acids, mono- and diglycerides of edible fatty acids, sugar esters of fatty acids, butylhydroxyanisole and -toluene, hexamethylenetetramine, amino acids, amino acid esters and all xanthine derivatives. Nevertheless, it is possible for a subject to manipulate the biological samples by transferring the marker to foreign urine and adding a substance that can break down the metabolizable substance.

The underlying problem of the invention is therefore to overcome the drawbacks present in the prior art and to permit a further improvement with respect to preventing manipulation of a biological sample to be examined for an analyte.

The underlying problem of the invention is solved by providing a composition comprising at least one essentially non-metabolizable marker substance and a dye.

Further, the present invention provides a method for identifying a biological sample of a mammal comprising: (a) Administration of a composition comprising at least one essentially non-metabolized marker substance and a dye to the mammal; (b) Drawing of a biological sample from the mammal; (c) Examination of the biological sample for the presence and/or amount of the at least one essentially non-metabolizable marker substance and optionally of the dye.

In another aspect the invention provides the optional examination of the identified biological sample for at least one specified analyte if the at least one essentially non-metabolizable marker substance or optionally the dye is/are detectable in the biological sample.

The idea of the present invention is therefore to find a possibility with which the biological sample being investigated can be marked with at least one essentially non-metabolizable marker substance and a dye in order to prevent this at least one essentially non-metabolizable marker substance from being removed again from the biological sample by methods available to the subject or which can be added to a foreign biological sample. The method is therefore suitable for monitoring methadone therapy and for doping controls. Advantageous inventive marker substances are generally characterized by a number of specific properties. These marker substances have no pharmacological side effects on the body of the mammal at the concentrations required for them to be detected as marker substances in blood, urine or other body fluids or body excretions according to the invention.

The term "marker substance" according to the present invention includes all substances that can be administered to a subject in order to permit marking of a biological sample. Marker substances should be detectable by known routine detection methods and also non-harmful to the mammal from a health standpoint. Advantageous marker substances are characterized by the fact that they are quickly absorbed via the intestinal mucosa and are excreted again from the subject by means of a body fluid or body excretion. It is also advantageous if these marker substances can be detected in the simplest possible manner by detection methods already established in chemical investigation laboratories, for example, common methods of clinical analytical chemistry. In one embodiment of the invention marker substances that are essentially non-metabolizable after absorption by the subject are used.

The at least one essentially non-metabolizable marker substance according to the present invention is a compound which is not metabolized in the mammal body, i.e. which is not converted in one or more different substances in the body, but is secreted essentially unchanged. The term "essentially" in this context means that at least 80%, at least 85%, at least 90%, at least 95%, at least 99% or 100% of the compound leaves the body of the mammal in unchanged form. According to the present invention the term "at least one essentially non-metabolizable marker substance" (in the following just "marker substance") also means that one marker substance, two marker substances, three marker substances, four marker substances, five marker substances or more marker substances are present in the inventive composition. In one embodiment two marker substances are present. In another embodiment three marker substances are present.

The marker substance can be chosen from carbohydrates, disaccharides, trisaccharides, tetrasaccharides, oligosaccharides, polysaccharides, isoprenoids, lipids, steroids, polyols, polyethylene glycols, acrylic polymers, poloxamers, polyoxyls, polysorbates, acesulfames, acetylated monoglycerides, butylparaben, povidone, copovidone, crospovidone, gelucire, hypomelloses, polycarbophils, polydextroses, tartaric acid or a salt thereof or their derivatives, but is not limited thereto. In one embodiment the marker substance is a polyethylene glycol. In another embodiment two, three, four or more polyethylene glycols having different molecular weights are used as marker substances. For example two different polyethylene glycols are used. In another example three different polyethylene glycols are used. In another example four or more polyethylene glycols are used. The polyethylene glycols used should therefore be distinguishable by chemical and/or physical analysis methods. The molecular weights of the polyethylene glycols are less than 5000 Da, 4000 Da, 3000 Da, 2000 Da, 1500 Da, 1000 Da, 900 Da, 800 Da, 700 Da, 600 Da, 500 Da or 400 Da. In one embodiment the molecular weights are greater than 100 Da, 150 Da, 200 Da, 250 Da, 300 Da, 400 Da or 500 Da. The polymer can have at least 2, 3, 4, 5, 6, 7, 8, 9, 10, 15, 20, 25, 30, 40, 50, 75, 100 or more repeating monomer units. The employed polyethylene glycols can be monodisperse and/or polydisperse. In one embodiment the polyethylene glycols are used in monodisperse form, for example, two or more monodisperse polyethylene glycols can be used with different molecular weight. Examples for usable polyethylene glycols are PEG 200, PEG 300, PEG 400, PEG 500, PEG 600, PEG 1000, PEG 1500 or their mixtures.

In one embodiment the marker substance can serve as solvent for the dye. For example, polyethylene glycol, like PEG 200, PEG 300, PEG 400 or PEG 500 or mixtures thereof, can function as solvent and simultaneously as marker substance.

Dyes according to the present invention are all dyes that are not risky for the health of mammals. In one embodiment food dyes are used. Food dyes are natural or synthetic compounds used in order to color foods, textiles or pharmaceutical products, to make children's paints safe or to impart certain properties to cosmetics. They are generally nonhazardous with respect to health, especially if they are not used above the permitted daily dose.

Examples of food dyes include but are not restricted to Allura red AC (E 129), aluminum (E 173), amaranth (E 123), anthocyanins (E 163), azorubine (E 122), betanin (E 162), brown FK (E 154), brown HT (E 155), brilliant blue FCF (E 133), brilliant black BN (E 151), calcium carbonate (E 170), canthaxanthine (E 161 g), carotene (E 160 a), annatto (norbixin) (E 160 b), capsanthin (E 160 c), lycopene (E 160 d), 8'-apo-β-caroten-8'-al (E 160 e), ethyl-8'-apo -β-caroten-8'-oate (E 160 f), quinoline yellow (E 104), chlorophyll (E 140), cochineal red A (E 124), curcumin (E 100), iron oxide (E 172), erythrosine (E 127), yellow orange S (E 110), gold (E 175), green S (E 142), indigotine (E 132), carmine (E 120), copper-containing complexes of chlorophylls and chlorophyllines (E 141), lactoflavin (E 101), litholrubin BK (E 180), lutein (E 161 b), patent blue V (E 131), vegetable charcoal (E 153), riboflavin (vitamin B2) (E 101), riboflavin-5-phosphate (E 101 a), safflower, silver (E 174), tartrazine (E 102), titanium dioxide (E 171), caramel color (E 150 a), caustic sulfite-caramel color (E 150 b), ammonia-caramel color (E 150 c), ammonium sulfite-caramel color (E 150 d) and zeaxanthin (E 161 h).

In one embodiment of the invention brilliant blue is used as dye. In another embodiment a mixture of two or more of the above mentioned food dyes is used, in which any combination of two, three, four, five, six or more food dyes is usable.

Food dyes are generally not metabolized so that they are detectable unaltered in the biological sample. They also have the property of coloring the oral mucosa on corresponding contact. The composition in the method according to the invention is therefore administered in a form in which it does not color the oral mucosa when used as prescribed. In one embodiment the composition is used in the form of a tablet or capsule, such as a gelatin capsule, whose outer shell prevents contact between the dye and the oral mucosa. However, should the subject chew such tablets in order to transfer the inventive composition to a foreign biological sample, for example, foreign urine, contact of the oral mucosa with the food dye and corresponding coloration of the oral mucosa occur.

In another embodiment the dye colors other body parts, for example, the hands, which can be used in order to remove the dye from the tablet or capsule in order to transfer it to a foreign biological sample, for example a foreign urine sample.

The dye is used in an amount which is sufficient to color the oral mucosa and/or other body parts if not used as specified.

If the sample was not manipulated, no discoloration of the oral mucosa (or of other body parts) can be observed. In another embodiment the administered dye is also detectable in the biological sample of the subject after intake of the inventive composition as prescribed.

The marker substance can be used in an amount sufficient so that it can be detected in the biological sample. The marker substance generally must be present in an amount so that it is still recognizable in the noise of the measurement methods. In addition, the marker concentration should be low enough so as not to interfere with detection of an analyte.

In another embodiment of the present invention one waits for specified period between step (a) and (b) of the method according to the invention, which is sufficient so that the marker substance reaches the location of sampling. In the case of sampling from a component separated from the sample donor, for example, during sampling from a body excretion, the period of time is understood to mean the period required until the marker substance is present in the separable component and this component is separated from the sample donor. Depending on the type of biological sample being taken, the period to be chosen is of different length. For example, the marker substance can be determined in urine at a different time than, for example in a blood sample. It is known to one with average skill in the art which periods must elapse in order to be able to detect the marker substance reliably in a biological sample. The waiting period can generally be determined empirically, but in most cases the corresponding values or methods for their determination are known in the prior art (van Rossum, J. M.: Kinetics of Drug Action. Handbook of Experimental Pharmacology, Vol. 47, Springer, Berlin, 1977; Forth, W.: General and Special Pharmacology and Toxicology, Bibliographic Institute & F. A. Brockhaus, Mannheim, 1988).

In addition at least one additional marker substance can be present in the inventive composition administered to the mammal. This additional marker substance may be present in the composition or may be administered separately. Use of a combination of different marker substances generally hampers the possibility of manipulating the biological sample. In addition, different marker substances can reach the location of sampling at different rates and the time to sampling can therefore be controlled, i.e., shortened. "At least one additional marker substance" according to the invention means at least one, at least two, at least three, at least four, at least five, at least six or more of the marker substances mentioned below.

The at least one additional marker substance can be chosen from carbohydrates, disaccharides, trisaccharides, tetrasaccharides, oligosaccharides, polysaccharides, isoprenoids, lipids, steroids, polyols, polyethylene glycols, acrylic polymers, poloxamers, polyoxyls, polysorbates, acesulfames, acetylated monoglycerides, butylparaben, povidone, copovidone, crospovidone, gelucire, hypomelloses, polycarbophils, polydextroses, tartaric acid or a salt thereof or their derivatives.

In another embodiment of the invention the at least one additional marker substance can be metabolizable and the detection of the non-metabolized form in the biological sample demonstrates a deception attempt. The term "metabolizable" according to the invention encompasses all compounds that are formed as a result of chemical conversion in the body of the subject or in the taken sample and thus form subsequent products differing from the original marker substance, in which, however, those subsequent products that cannot be exclusively attributed to conversion of a specific marker substance in the subject's body or in the taken biological sample are excluded.

Possible metabolizable substances can be sucrose or benzoic acid and 4-hydroxybenzoic acid derivatives, especially their alkyl esters, acetic acid, fatty acid, lactic acid and tartaric acid esters of glycerol, propylene glycol esters of fatty acids, mono- and diglycerides of edible fatty acids, sugar esters of fatty acids, butylhydroxyanisole and -toluene, hexamethylenetetramine, amino acids, amino acid esters and all xanthine derivatives, but are not limited to.

The usable saccharides can include, but are not restricted to arabinose, erythrulose, myoinositol, cis-inositol, mannitol, sorbose, rhamnose, sorbitol, xylose and xylulose.

Further, the inventive method is suitable for the detection of an analyte in a biological sample of a mammal, i.e. a biological sample from a subject that has been positively identified may be examined for at least one particular analyte. Mammals include, but are not limited to, humans, cattle, pigs, chickens, sheep or horses. In one embodiment the mammal is a human.

Administration of the composition can occur in different ways. "Administration" means the introduction of the composition, i.e. of the marker substance (and optionally of the at least one additional marker substance) into the body of the sample donor. The marker substance(s) according to the invention can be administered to the sample donor orally, but the invention is not restricted to this. It is particularly preferred that the marker substance(s) are absorbed via the digestive tract. In one embodiment no metabolization of the marker substance(s) occurs during absorption. In another embodiment at least one of the additional marker substances is metabolizable.

In one embodiment of the invention in case several marker substances are used, these should be administered simultaneously, in which case it is possible by a combination of marker substances to develop a specific numerical code pertaining to a sample. For example, in order to increase manipulation safety a combination of at least two, at least three, at least four or at least five marker substances can be administered simultaneously. Each combination of mentioned marker substances (i.e. marker substance(s) and optional at least one additional marker substance) is usable in the present invention. When a total number of n marker substances are used there are $2^n-1$ different combinations in a dual numerical system. Manipulation of the sample by the subject is therefore additionally hampered to impossible, since the subject must know the chemical nature of the marker substance, the numerical code for his biological sample and the sequence of marker substances according to which the code is constructed.

"Biological sample" means the components of a mammal intended for analytical investigation. For example, the biological sample can be blood, urine, stool, secretions from the salivary, mammary, lacrimal and sweat glands, wherein additional body fluids or body excretions can be used as biological sample. In one embodiment of the invention the biological sample is urine. In one embodiment of the invention the biological sample is blood. The components forming the sample can be both components of a mammal organism still present in the mammal at the time of sampling or also former components of the mammal.

Sampling occurs by taking part of the sample into a sample container and it is then ready for further examination. During examination of human urine samples the samples can generally be furnished by the subjects themselves by merely handing the subjects a sample container.

During examination of urine samples the composition is administered, for example, orally to the subjects in the form of a tablet, for example, administered orally about 30 to 60 minutes before urine is furnished.

Depending on the type of sample and the marker substance(s) (i.e. marker substance(s) and optional one additional marker substance) which should be detected, the sample is worked up before the analysis method. The workup steps can include centrifuging to separate solid, undissolved substances in a liquid sample, for example urine or blood, concentration by ion exchange chromatography, using centricons, precipitation with appropriate reagents, like ammonium sulfate, adjustment of the pH value required for the analysis method and additional workup steps known to one skilled in the art.

For detection of presence or absence of the marker substance(s) and optionally the dye in a sample, a number of enzymatic, immunological, mass spectrometric and electrophoretic detection methods as well as their combinations are available. For example, analysis of the at least one marker substance and/or analyte can occur by gas chromatography (GC), gas chromatography/mass spectrometry (GC/MS), gas chromatography/tandem mass spectrometry (GC/MS/MS), high performance liquid chromatography (HPLC), high performance liquid chromatography/mass spectrometry (HPLC/MS) and/or high performance liquid chromatography/tandem mass spectrometry (HPLC/MS/MS). Instead of HPLC, LC can also be used. With these methods liquid samples or samples that were converted to liquid as a result of workup can be investigated with considerable time economy. At the same time these detection methods permit a high degree of automation so that a number of samples can be analyzed in a short time. In case the chromatograms and any mass spectrometric fraction samples of reference substances are already present in the computer evaluation unit, the actual detection of the marker substance(s) is also greatly simplified.

In one embodiment of the invention the biological sample is examined for the presence and/or the amount of the marker substance, wherein the marker substance is one, two, three or more of the above-mentioned polyethylene glycols.

If it is found as a result of evaluation of the employed analysis method that the originally administered marker substance or the marker substance and the at least one additional marker substance (or the metabolized form thereof) is present in the investigated sample, this permits distinct assignment of this sample to the subject. If this requirement is met, i.e., the sample comes from the subject being examined, the investigation of the sample, or, as an alternative, of a second sample, for at least one specific analyte may be carried out.

"Analyte" is understood to mean at least one chemical substance, in which knowledge concerning the presence of the analyte or also its concentration in the sample permits a conclusion of a previous, expected or instantaneous state of the sample donor. For example, based on knowledge of the concentration of an analyte, for example, glucose concentration in urine of a urine sample, which was determined generally enzymatically by glucose oxidase (GOD) or hexokinase, a conclusion can be made concerning incorrectly functioning and therefore incomplete resorption of glucose from the urine by the kidney tubuli (glucosuria) in a subject. Analytes can also be intoxicants, drugs or metabolites of the aforementioned substances, whose detection in the sample permits a conclusion concerning the behavior or treatment of the subject. For example, the analyte can be chosen from the group consisting of heroin, methadone, cocaine, THC and their derivatives, drugs chosen from the group of barbiturates and their derivatives, nicotine, alcohol or a doping agent on the list of doping agents.

In addition to use of the method according to the invention in human medicine, a number of additional applications exist in the veterinary field and in agriculture. The method can advantageously be employed in monitoring compliance with regulations on use of feed additives in agricultural large-scale livestock raising.

For example, if samples recovered from fattening pigs are to be investigated for the presence of growth hormones or antibiotics or their metabolites, by using the method according to the invention the problem of manipulation of the samples being investigated by the owner of a fattening pig herd can be avoided. Marker substances are advantageous in particular here, which are present for a long period (ideally the entire fattening time) in the body but which are continuously present in detectable amounts, for example, in a body excretion. Marker substances that can be administered as a depot active ingredient to the animal are therefore advantageous and, as a result, delayed but continuously occurring resorption takes place though the intestinal mucosa and the marker substance(s) is/are therefore detectable over a longer period in a body excretion, like animal feces. Particularly suitable samples are those samples with which both the investigation for marker substance(s) and also detection and concentration determination of at least one analyte occurs.

One embodiment of the present invention is directed to a tablet, capsule, such as a gelatin capsule, or a similar dosage form, comprising the inventive composition. For example, the tablet or capsule may comprise the marker substance as well as the dye or the marker substance as well as the dye and at least one of the above-mentioned additional marker substances. In one embodiment of the invention the tablet or capsule comprises, besides the dye, a polyethylene glycol or two polyethylene glycols or three polyethylene glycols having different molecular weights. In one embodiment a computer-readable code is directly present on the dosage form, i.e., for example, on the tablet or capsule. For example, the code may be a bar code.

Another embodiment of the present invention is directed toward a kit for performing the described method for sample identification in a mammal, wherein the kit according to the invention includes the inventive composition in a suitable dosage form, as well as optional means for administration of the composition to the mammal. In another embodiment the kit comprises the inventive composition and at least one additional marker substance in a suitable dosage form.

It is particularly advantageous if this kit also contains at least one reference substance for detection of the marker substance(s).

It is particularly advantageous that the dosage form included in the kit is provided with a computer-readable code. Suitable dosage forms are tablets, capsules or the like. Kits that are provided for marking of urine samples in methadone patients preferably contain tablets, capsules or similar dosage forms in which both the amount of methadone to be administered and the inventive composition and optionally one additional marker substance are present together. In one embodiment the computer-readable code is located directly on the dosage form, i.e. on the tablet or capsule. For example, the code may be a bar code.

In one embodiment of the kit according to the invention contains several reference substances by means of which the marker substance or the marker substance and the at least one additional marker substance can be simply identified during chromatographic analysis of the biological sample, such as a urine sample or a blood sample.

For example, during examination of the urine sample of a patient treated with methadone, an ampule can additionally be present in the kit according to the invention, which contains a marker substance or mixture thereof dissolved in an appropriate solvent according to the chosen chromatographic method, in which case this marker substance or the mixture correspond exactly to the one present in the corresponding methadone tablets.

During GC analysis it can be established very quickly and reliably by a subsequent run on the same GC column based on the chromatography peak of the marker substances whether the investigated urine sample comes from the patient treated with methadone.

The invention claimed is:
1. A method for identifying a biological sample of a mammal, the method comprising:
administering to the mammal a capsule comprising a capsule composition and a capsule outer shell, wherein the capsule composition comprising at least two essentially non-metabolizable marker substances and a dye, wherein the capsule composition administered to the mammal comprises an amount of the dye effective to color oral mucosa of the mammal, the at least two essentially nonmetabolizable marker substances comprise a plurality of polyethylene glycols (PEGs) with different molecular weight relative to each other, wherein the molecular weight of each of the plurality of polyethylene glycols is less than 5000 kDa;
the capsule outer shell preventing contact between the dye and the oral mucosa of the mammal;

if the capsule is chewed, the capsule outer shell allowing contact between the dye and the oral mucosa of the mammal;

collecting a biological sample from the mammal;

examining the biological sample for the presence and/or amount of the at least two essentially non-metabolizable marker substances and optionally of the dye; and examining the biological sample for at least one specified analyte selected from the group consisting of illegal drugs, a barbiturate, a barbiturate derivative, nicotine, alcohol, a doping agent and combinations thereof.

2. The method of claim 1, wherein the dye is chosen from the group consisting of Allura Red AC (E 129), aluminum (E 173), amaranth (E 123), anthocyanins (E 163), azorubin (E 122), betanin (E 162), brown FK (E 154), brown HT (E 155), brilliant blue FCF (E 133), brilliant black BN (E 151), calcium carbonate (E 170), canthaxanthine (E 161 g), carotene (E 160 a), annatto (N orbixin) (E 160 b), capsanthin (E 160 c), lycopene (E 160 d), 8'-apo-β-ca rotenal-81-al (E 160 e), ethyl-8'apo-β-carotenal-8'oate (E 160 f), quinoline yellow (E 104), chlorophyll (E 140), cochenille red A (E 124), curcumin (E 100), iron oxide (E 172), erythrosine (E 127), yellow orangeS (E 110), gold (E175), greenS (E 142), indigotine (E 132), cochineal (E 120), copper-containing complexes of chlorophylls and chlorophyllines (E 141), lactoflavin (E 101), litholrubin BK (E 180), lutein (E 161 b), patent blue V (E 131), vegetable charcoals (E 153), riboflavin (vitamin B2) (E 101), riboflavin-5- phosphate (E 101 a), safflower, silver (E 174), tartrazine (E 102), titanium dioxide (E 171), caramel color (E 150 a), caustic sulfite-caramel color (E 150 b), ammonia-caramel color (E 150 c), ammonium sulfite- caramel color (E 150 d) and zeaxanthin (E 161 h).

3. The method of claim 1, the capsule composition further comprising at least one additional marker substance.

4. The method of claim 3, wherein the at least one additional marker substance is metabolizable.

5. The method of claim 1, wherein the plurality of polyethylene glycols (PEGs) are two polyethylene glycols (PEGs) present in an amount sufficient for detection in a biological sample from a mammal upon ingestion of the capsule by the mammal.

6. The method of claim 5, wherein the at least two polyethylene glycols each have different molecular weight of less than 4000 Da.

7. The method of claim 1, wherein the capsule composition contains a computer-readable code.

8. The method of claim 1, wherein the biological sample is urine.

9. The method of claim 1, wherein the dye is present in an amount sufficient to color oral mucosa of a first mammal if the first mammal attempts to transfer the non-metabolizable marker to a biological sample from a second mammal.

10. The method of claim 9, wherein the capsule is configured such that the dye does not color the oral mucosa of the first mammal upon oral administration of the capsule to the first mammal.

11. The method of claim 1, wherein the dye is in solution.

12. The method of claim 1, wherein the at least two essentially non-metabolizable marker substances serve as solvent for the dye.

13. The method of claim 1, wherein the capsule composition does not contain riboflavin.

\* \* \* \* \*